US006998122B1

(12) United States Patent
Gerlitz et al.

(10) Patent No.: US 6,998,122 B1
(45) Date of Patent: Feb. 14, 2006

(54) PROTEIN C DERIVATIVES

(75) Inventors: Bruce Edward Gerlitz, Indianapolis, IN (US); Bryan Edward Jones, Carmel, IN (US); David Thompson Berg, Beech Grove, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/719,911

(22) PCT Filed: Apr. 13, 2000

(86) PCT No.: PCT/US00/08722

§ 371 (c)(1),
(2), (4) Date: Dec. 14, 2000

(87) PCT Pub. No.: WO00/66754

PCT Pub. Date: Nov. 9, 2000

Related U.S. Application Data

(60) Provisional application No. 60/131,801, filed on Apr. 30, 1999.

(51) Int. Cl.
*A61K 38/48* (2006.01)
*C12N 9/64* (2006.01)
*C12N 15/00* (2006.01)
*C12N 5/00* (2006.01)
*C07H 21/04* (2006.01)

(52) U.S. Cl. ............... 424/94.64; 435/226; 435/320.1; 435/325; 536/23.2

(58) Field of Classification Search ............... 435/219, 435/320.1, 325, 455, 440, 69.1, 226; 424/94.1, 424/94.64; 536/23.1, 23.2

See application file for complete search history.

(56) References Cited

U.S. PATENT DOCUMENTS

| | | | |
|---|---|---|---|
| 4,992,373 A | | 2/1991 | Bang et al. |
| 5,196,322 A | | 3/1993 | Bang et al. |
| 5,270,178 A | * | 12/1993 | Gerlitz et al. ............... 435/69.1 |
| 5,358,932 A | | 10/1994 | Foster et al. |
| 5,453,373 A | * | 9/1995 | Gerlitz et al. ............... 435/226 |
| 5,460,953 A | | 10/1995 | Gerlitz et al. |
| 5,837,843 A | | 11/1998 | Smirnov et al. |
| 5,847,085 A | | 12/1998 | Esmon et al. |
| 6,017,882 A | | 1/2000 | Nelsestuen |
| 2003/0022354 A1 | * | 1/2003 | Gerlitz et al. ............ 435/240.2 |

FOREIGN PATENT DOCUMENTS

| | | |
|---|---|---|
| EP | 0 296 413 | 9/1988 |
| EP | 0 354 504 | 5/1989 |
| EP | 0 443 874 | 2/1991 |
| JP | 03 072877 A | 3/1991 |
| WO | WO 91/09960 | 7/1991 |
| WO | WO 98/20118 | 5/1998 |
| WO | WO 98/44000 | 10/1998 |
| WO | WO 99/20767 | 4/1999 |
| WO | WO 00/66753 | 11/2000 |
| WO | WO 00/66754 | 11/2000 |

OTHER PUBLICATIONS

U.S. Appl. No. 09/497,591, filed Feb. 3, 2000, Nelsestuen.
U.S. Appl. No. 10/168,407, Gerlitz, et al.
U.S. Appl. No. 10/129,893, Gerlitz, et al.
U.S. Appl. No. 10/182,263, Gerlitz, et al.
Database Swall Online!, "Vitamin K–dependent protein C precursor" *European Bioinformatics Institute & Swiss Institute for Bioinformatics*, 1986.
Grinnell, B., et al., "Glycosylation of Human protein C Affects Its Secretion, Processing, Functional Activities and Activation by Thrombin," *Journal of Biological Chemistry*, vol. 266, No. 15, 1991, pp. 9778–9785.
Rezaie AR, et al., "Conversion of Glutamic Acid 192 to Glutamine in Activated Protein C Changes the Substrate Specificity and Increases Reactivity toward Macromolecular Inhibitors," *Journal of Biological Chemistry*, vol. 268, No. 27, 1993, pp. 19943–19948.
Mather T., et al., "The 2.8A crystal structure of Gla–domainless activated protein C," *The Embo Journal*, vol. 15, No. 24, 1996, pp. 6822–6831.
Tsiang M., et al., "Protein Engineering Thrombin for Optimal Specificity and Potency of Anticoagulant Activity in Vivo," *Biochemistry*, vol. 35, No. 51, 1996, pp. 16449–16457.
Rezaie AR, "Role of Residue 99 at the S2 Subsite of Factor Xa and Activated Protein C in Enzyme Specificity," *Journal of Biological Chemistry, The American Society of Biological Chemists, Inc.*, vol. 271, No. 39, 1996, pp. 23807–23814.
Kurz K., et al., "Antithrombic Efficacy in the Guinea Pig of a Derivative of Human Protein C with Enhanced Activation by Thrombin", *Blood*, vol. 89, No. 2, 1997, pp. 534–540.
Shen L., et al., "Enhancing the Activity of Protein C by Mutagenesis to Improve the Membrane–Binding Site: Studies Related to Proline–10" *Biochemistry, American Chemical Society*, vol. 36, No. 51, 1997, pp. 16025–16031.
Shen L., et al., "Enhancement of Human Protein C Function by Site–directed Mutagenesis of the γ–Carboxyglutamic Acid Domain," *Journal of Biological Chemistry, American Society of Biological Chemists*, vol. 273, No. 47, 1998, pp. 31086–31091.
McDonald J., et al., "Comparison of Naturally Occurring Vitamin K–dependent Proteins: Correlation of Amino Acid Sequences and Membrane Binding Properties Suggests a Membrane Contact Site," *Biochemistry*, vol. 36, No. 17, 1997, pp. 5120–5127.
Zhang L., et al., "The Contributions of Individual γ–Carboxyglutamic Acid Residues in the Calcium–dependent Binding of Recombinant Human Protein C to Acidic Phospholipid Vesicles," *The Journal of Biological Chemistry*, vol. 268, No. 16, 1993, pp. 12040–12045.

* cited by examiner

*Primary Examiner*—Rebecca Prouty
*Assistant Examiner*—Malgorzata A Walicka
(74) *Attorney, Agent, or Firm*—Gerald P. Keleher; Brian P. Barrett; Lynn D. Apelgren

(57) ABSTRACT

Novel protein C derivatives are described. These polypeptides retain the biological activity of the wild-type human protein C with substantially longer half-lives in human blood. These polypeptides will require either less frequent administration and/or smaller dosage than wild-type human protein C in the treatment of vascular occlusive disorders, hypercoagulable states, thrombotic disorders and disease states predisposing to thrombosis.

39 Claims, 5 Drawing Sheets

SEQUENCE LISTING

```
<160> NUMBER OF SEQ ID NOS: 10

<210> SEQ ID NO 1
<211> LENGTH: 419
<212> TYPE: PRT
<213> ORGANISM: Homo sapiens

<400> SEQUENCE: 1
```

Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
        50                  55                  60

Gly His Gly Thr Cys Ile Asp Gly Ile Gly Ser Phe Ser Cys Asp Cys

```
            65                  70                  75                  80
Arg Ser Gly Trp Glu Gly Arg Phe Cys Gln Arg Glu Val Ser Phe Leu
                        85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
                115                 120                 125

Asp Leu Leu Gln Cys His Pro Ala Val Lys Phe Pro Cys Gly Arg Pro
            130                 135                 140

Trp Lys Arg Met Glu Lys Lys Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
                180                 185                 190

Lys Leu Ala Cys Gly Ala Val Leu Ile His Pro Ser Trp Val Leu Thr
                195                 200                 205

Ala Ala His Cys Met Asp Glu Ser Lys Lys Leu Leu Val Arg Leu Gly
            210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
                275                 280                 285

Asn Gln Ala Gly Gln Glu Thr Leu Val Thr Gly Trp Gly Tyr His Ser
            290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 2
<211> LENGTH: 461
<212> TYPE: PRT
<213> ORGANISM: Homo sapiens

<400> SEQUENCE: 2

Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Ser Glu Arg
```

-continued

```
                20                  25                  30
Ala His Gln Val Leu Arg Ile Arg Lys Arg Ala Asn Ser Phe Leu Glu
         35                  40                  45

Glu Leu Arg His Ser Ser Leu Glu Arg Glu Cys Ile Glu Glu Ile Cys
 50                  55                  60

Asp Phe Glu Glu Ala Lys Glu Ile Phe Gln Asn Val Asp Asp Thr Leu
 65                  70                  75                  80

Ala Phe Trp Ser Lys His Val Asp Gly Asp Gln Cys Leu Val Leu Pro
                 85                  90                  95

Leu Glu His Pro Cys Ala Ser Leu Cys Cys Gly His Gly Thr Cys Ile
             100                 105                 110

Asp Gly Ile Gly Ser Phe Ser Cys Asp Cys Arg Ser Gly Trp Glu Gly
             115                 120                 125

Arg Phe Cys Gln Arg Glu Val Ser Phe Leu Asn Cys Ser Leu Asp Asn
 130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                 165                 170                 175

Pro Ala Val Lys Phe Pro Cys Gly Arg Pro Trp Lys Arg Met Glu Lys
             180                 185                 190

Lys Arg Ser His Leu Lys Arg Asp Thr Glu Asp Gln Glu Asp Gln Val
             195                 200                 205

Asp Pro Arg Leu Ile Asp Gly Lys Met Thr Arg Arg Gly Asp Ser Pro
 210                 215                 220

Trp Gln Val Val Leu Leu Asp Ser Lys Lys Leu Ala Cys Gly Ala
225                 230                 235                 240

Val Leu Ile His Pro Ser Trp Val Leu Thr Ala Ala His Cys Met Asp
             245                 250                 255

Glu Ser Lys Lys Leu Leu Val Arg Leu Gly Glu Tyr Asp Leu Arg Arg
             260                 265                 270

Trp Glu Lys Trp Glu Leu Asp Leu Asp Ile Lys Glu Val Phe Val His
             275                 280                 285

Pro Asn Tyr Ser Lys Ser Thr Thr Asp Asn Asp Ile Ala Leu Leu His
 290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                 325                 330                 335

Thr Leu Val Thr Gly Trp Gly Tyr His Ser Ser Arg Glu Lys Glu Ala
             340                 345                 350

Lys Arg Asn Arg Thr Phe Val Leu Asn Phe Ile Lys Ile Pro Val Val
             355                 360                 365

Pro His Asn Glu Cys Ser Glu Val Met Ser Asn Met Val Ser Glu Asn
             370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                 405                 410                 415

Val Gly Leu Val Ser Trp Gly Glu Gly Cys Gly Leu Leu His Asn Tyr
             420                 425                 430

Gly Val Tyr Thr Lys Val Ser Arg Tyr Leu Asp Trp Ile His Gly His
             435                 440                 445
```

```
Ile Arg Asp Lys Glu Ala Pro Gln Lys Ser Trp Ala Pro
    450                 455                 460
```

<210> SEQ ID NO 3
<211> LENGTH: 419
<212> TYPE: PRT
<213> ORGANISM: Homo sapiens

<400> SEQUENCE: 3

```
Ala Asn Ser Phe Leu Glu Glu Leu Arg His Ser Ser Leu Glu Arg Glu
  1               5                  10                  15

Cys Ile Glu Glu Ile Cys Asp Phe Glu Glu Ala Lys Glu Ile Phe Gln
             20                  25                  30

Asn Val Asp Asp Thr Leu Ala Phe Trp Ser Lys His Val Asp Gly Asp
         35                  40                  45

Gln Cys Leu Val Leu Pro Leu Glu His Pro Cys Ala Ser Leu Cys Cys
     50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Ser Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
```

```
                      355                 360                 365
His Gly Thr Trp Phe Leu Val Gly Leu Val Ser Trp Gly Glu Gly Cys
        370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro

<210> SEQ ID NO 4
<211> LENGTH: 419
<212> TYPE: PRT
<213> ORGANISM: Homo sapiens

<400> SEQUENCE: 4

Ala Asn Ser Phe Leu Glu Glu Leu Arg His Ser Leu Glu Arg Glu
1               5                   10                  15
Cys Ile Glu Glu Ile Cys Asp Phe Glu Glu Ala Lys Glu Ile Phe Gln
                20                  25                  30
Asn Val Asp Asp Thr Leu Ala Phe Trp Ser Lys His Val Asp Gly Asp
            35                  40                  45
Gln Cys Leu Val Leu Pro Leu Glu His Pro Cys Ala Ser Leu Cys Cys
    50                  55                  60
Gly His Gly Thr Cys Ile Asp Gly Ile Gly Ser Phe Ser Cys Asp Cys
65                  70                  75                  80
Arg Ser Gly Trp Glu Gly Arg Phe Cys Gln Arg Glu Val Ser Phe Leu
                85                  90                  95
Asn Cys Ser Leu Asp Asn Gly Gly Cys Thr His Tyr Cys Leu Glu Glu
            100                 105                 110
Val Gly Trp Arg Arg Cys Ser Cys Ala Pro Gly Tyr Lys Leu Gly Asp
        115                 120                 125
Asp Leu Leu Gln Cys His Pro Ala Val Lys Phe Pro Cys Gly Arg Pro
130                 135                 140
Trp Lys Arg Met Glu Lys Lys Arg Ser His Leu Lys Arg Asp Thr Glu
145                 150                 155                 160
Asp Gln Glu Asp Gln Val Asp Pro Arg Leu Ile Asp Gly Lys Met Thr
                165                 170                 175
Arg Arg Gly Asp Ser Pro Trp Gln Val Val Leu Leu Asp Ser Lys Lys
            180                 185                 190
Lys Ser Ala Cys Gly Ala Val Leu Ile His Pro Ser Trp Val Leu Thr
        195                 200                 205
Ala Ala His Cys Met Asp Glu Ser Lys Lys Leu Leu Val Arg Leu Gly
    210                 215                 220
Glu Tyr Asp Leu Arg Arg Trp Glu Lys Trp Glu Leu Asp Leu Asp Ile
225                 230                 235                 240
Lys Glu Val Phe Val His Pro Asn Tyr Ser Lys Ser Thr Ser Asp Asn
                245                 250                 255
Asp Ile Ala Leu Leu His Leu Ala Gln Pro Ala Thr Leu Ser Gln Thr
            260                 265                 270
Ile Val Pro Ile Cys Leu Pro Asp Ser Gly Leu Ala Glu Arg Glu Leu
        275                 280                 285
Asn Gln Ala Gly Gln Glu Thr Leu Val Thr Gly Trp Gly Tyr His Ser
    290                 295                 300
Ser Arg Glu Lys Glu Ala Lys Arg Asn Arg Thr Phe Val Leu Asn Phe
```

```
                305                 310                 315                 320
Ile Lys Ile Pro Val Val Pro His Asn Glu Cys Ser Glu Val Met Ser
                    325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 5
<211> LENGTH: 419
<212> TYPE: PRT
<213> ORGANISM: Homo sapiens

<400> SEQUENCE: 5

Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Ala Ala Cys Gly Ala Val Leu Ile His Pro Ser Trp Val Leu Thr
    195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Ser Asp Asn
                245                 250                 255

Asp Ile Ala Leu Leu His Leu Ala Gln Pro Ala Thr Leu Ser Gln Thr
```

```
                260                 265                 270
Ile Val Pro Ile Cys Leu Pro Asp Ser Gly Leu Ala Glu Arg Glu Leu
                275                 280                 285
Asn Gln Ala Gly Gln Glu Thr Leu Val Thr Gly Trp Gly Tyr His Ser
                290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
                340                 345                 350
Gln Asp Ala Cys Glu Gly Asp Ser Gly Gly Pro Met Val Ala Ser Phe
                355                 360                 365
His Gly Thr Trp Phe Leu Val Gly Leu Val Ser Trp Gly Glu Gly Cys
                370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro

<210> SEQ ID NO 6
<211> LENGTH: 1260
<212> TYPE: DNA
<213> ORGANISM: Homo sapiens

<400> SEQUENCE: 6
gccaactcct tcctggagga gctccgtcac agcagcctgg agcgggagtg catagaggag      60
atctgtgact tcgaggaggc caaggaaatt tccaaaatg tggatgacac actggccttc     120
tggtccaagc acgtcgacgg tgaccagtgc ttggtcttgc ccttggagca cccgtgcgcc     180
agcctgtgct gcgggcacgg cacgtgcatc gacggcatcg gcagcttcag ctgcgactgc     240
cgcagcggct gggagggccg cttctgccag cgcgaggtga gcttcctcaa ttgctcgctg     300
gacaacggcg gctgcacgca ttactgccta gaggaggtgg gctggcggcg ctgtagctgt     360
gcgcctggct acaagctggg ggacgacctc ctgcagtgtc accccgcagt gaagttccct     420
tgtgggaggc cctggaagcg gatggagaag aagcgcagtc acctgaaacg agacacagaa     480
gaccaagaag accaagtaga tccgcggctc attgatggga gatgaccag gcggggagac     540
agcccctggc aggtggtcct gctggactca agaagaagc tggcctgcgg ggcagtgctc     600
atccacccct cctgggtgct gacagcggcc cactgcatgg atgagtccaa gaagctcctt     660
gtcaggcttg gagagtatga cctgcggcgc tgggagaagt gggagctgga cctggacatc     720
aaggaggtct tcgtccaccc caactacagc aagagcacca ccgacaatga tcgcactg     780
ctgcacctgg cccagcccgc cacctctcg cagaccatag tgcccatctg cctcccggac     840
agcggccttg cagagcgcga gctcaatcag gccggccagg agaccctcgt gacgggctgg     900
ggctaccaca gcagccgaga gaaggaggcc aagagaaacc gcaccttcgt cctcaacttc     960
atcaagattc ccgtggtccc gcacaatgag tgcagcgagg tcatgagcaa catggtgtct    1020
gagaacatgc tgtgtgcggg catcctcggg gaccggcagg atgcctgcga gggcgacagt    1080
ggggggccca tggtcgcctc cttccacggc acctggttcc tggtgggcct ggtgagctgg    1140
ggtgagggct gtgggctcct tcacaactac ggcgtttaca ccaaagtcag ccgctacctc    1200
```

```
gactggatcc atgggcacat cagagacaag gaagccccc agaagagctg ggcaccttag    1260
```

<210> SEQ ID NO 7
<211> LENGTH: 1386
<212> TYPE: DNA
<213> ORGANISM: Homo sapiens

<400> SEQUENCE: 7

```
atgtggcagc tcacaagcct cctgctgttc gtggccacct ggggaatttc cggcacacca      60
gctcctcttg actcagtgtt ctccagcagc gagcgtgccc accaggtgct gcggatccgc     120
aaacgtgcca actccttcct ggaggagctc cgtcacagca gcctggagcg ggagtgcata     180
gaggagatct gtgacttcga ggaggccaag gaaattttcc aaaatgtgga tgacacactg     240
gccttctggt ccaagcacgt cgacggtgac cagtgcttgg tcttgccctt ggagcacccg     300
tgcgccagcc tgtgctgcgg gcacggcacg tgcatcgacg catcggcag cttcagctgc     360
gactgccgca gcggctggga gggccgcttc tgccagcgcg aggtgagctt cctcaattgc     420
tcgctggaca acggcggctg cacgcattac tgcctagagg aggtgggctg gcggcgctgt     480
agctgtgcgc ctggctacaa gctggggggac gacctcctgc agtgtcaccc cgcagtgaag     540
ttcccttgtg ggaggccctg gaagcggatg gagaagaagc gcagtcacct gaaacgagac     600
acagaagacc aagaagacca gtagatccg cggctcattg atgggaagat gaccaggcgg     660
ggagacagcc cctggcaggt ggtcctgctg gactcaaaga agaagctggc ctgcggggca     720
gtgctcatcc accctcctg gtgctgaca gcggcccact gcatggatga gtccaagaag     780
ctccttgtca ggcttggaga gtatgacctg cggcgctggg agaagtggga gctggacctg     840
gacatcaagg aggtcttcgt ccaccccaac tacagcaaga gcaccaccga caatgacatc     900
gcactgctgc acctggccca gcccgccacc ctctcgcaga ccatagtgcc catctgcctc     960
ccggacagcg gccttgcaga gcgcgagctc aatcaggccg ccaggagac cctcgtgacg    1020
ggctggggct accacagcag ccgagagaag gaggccaaga gaaaccgcac cttcgtcctc    1080
aacttcatca gattcccgt ggtcccgcac aatgagtgca gcgaggtcat gagcaacatg    1140
gtgtctgaga acatgctgtg tgcgggcatc ctcgggggacc ggcaggatgc ctgcgagggc    1200
gacagtgggg ggcccatggt cgcctccttc acggcacct ggttcctggt gggcctggtg    1260
agctggggtg agggctgtgg gctccttcac aactacggcg tttacaccaa agtcagccgc    1320
tacctcgact ggatccatgg gcacatcaga gacaaggaag cccccagaa gagctgggca    1380
ccttag                                                                1386
```

<210> SEQ ID NO 8
<211> LENGTH: 1386
<212> TYPE: DNA
<213> ORGANISM: Homo sapiens

<400> SEQUENCE: 8

```
atgtggcagc tcacaagcct cctgctgttc gtggccacct ggggaatttc cggcacacca      60
gctcctcttg actcagtgtt ctccagcagc gagcgtgccc accaggtgct gcggatccgc     120
aaacgtgcca actccttcct ggaggagctc cgtcacagca gcctggagcg ggagtgcata     180
gaggagatct gtgacttcga ggaggccaag gaaattttcc aaaatgtgga tgacacactg     240
gccttctggt ccaagcacgt cgacggtgac cagtgcttgg tcttgccctt ggagcacccg     300
tgcgccagcc tgtgctgcgg gcacggcacg tgcatcgacg catcggcag cttcagctgc     360
gactgccgca gcggctggga gggccgcttc tgccagcgcg aggtgagctt cctcaattgc     420
```

```
tcgctggaca acggcggctg cacgcattac tgcctagagg aggtgggctg gcggcgctgt    480
agctgtgcgc ctggctacaa gctgggggac gacctcctgc agtgtcaccc cgcagtgaag    540
ttcccttgtg ggaggccctg gaagcggatg gagaagaagc gcagtcacct gaaacgagac    600
acagaagacc aagaagacca agtagatccg cggctcattg atgggaagat gaccaggcgg    660
ggagacagcc cctggcaggt ggtcctgctg gactcaaaga agaagtccgc ctgcggggca    720
gtgctcatcc acccctcctg ggtgctgaca gcggcccact gcatggatga gtccaagaag    780
ctccttgtca ggcttggaga gtatgacctg cggcgctggg agaagtggga gctggacctg    840
gacatcaagg aggtcttcgt ccaccccaac tacagcaaga gcaccaccga caatgacatc    900
gcactgctgc acctggccca gcccgccacc ctctcgcaga ccatagtgcc catctgcctc    960
ccggacagcg gccttgcaga gcgcgagctc aatcaggccg gccaggagac cctcgtgacg   1020
ggctggggct accacagcag ccgagagaag gaggccaaga gaaaccgcac cttcgtcctc   1080
aacttcatca gattcccgt ggtcccgcac aatgagtgca gcgaggtcat gagcaacatg   1140
gtgtctgaga acatgctgtg tgcgggcatc ctcgggacc ggcaggatgc ctgcgagggc   1200
gacagtgggg ggcccatggt cgcctccttc cacggcacct ggttcctggt gggcctggtg   1260
agctggggtg agggctgtgg gctccttcac aactacggcg tttacaccaa agtcagccgc   1320
tacctcgact ggatccatgg gcacatcaga gacaaggaag ccccccagaa gagctgggca   1380
ccttag                                                               1386
```

<210> SEQ ID NO 9
<211> LENGTH: 1386
<212> TYPE: DNA
<213> ORGANISM: Homo sapiens

<400> SEQUENCE: 9

```
atgtggcagc tcacaagcct cctgctgttc gtggccacct ggggaatttc cggcacacca     60
gctcctcttg actcagtgtt ctccagcagc gagcgtgccc accaggtgct gcggatccgc    120
aaacgtgcca actccttcct ggaggagctc cgtcacagca gctggagcg ggagtgcata    180
gaggagatct gtgacttcga ggaggccaag gaaattttcc aaaatgtgga tgacacactg    240
gccttctggt ccaagcacgt cgacggtgac cagtgcttgg tcttgccctt ggagcacccg    300
tgcgccagcc tgtgctgcgg gcacggcacg tgcatcgacg gcatcggcag cttcagctgc    360
gactgccgca gcggctggga gggccgcttc tgccagcgcg aggtgagctt cctcaattgc    420
tcgctggaca acggcggctg cacgcattac tgcctagagg aggtgggctg gcggcgctgt    480
agctgtgcgc ctggctacaa gctgggggac gacctcctgc agtgtcaccc cgcagtgaag    540
ttcccttgtg ggaggccctg gaagcggatg gagaagaagc gcagtcacct gaaacgagac    600
acagaagacc aagaagacca agtagatccg cggctcattg atgggaagat gaccaggcgg    660
ggagacagcc cctggcaggt ggtcctgctg gactcaaaga agaagtccgc ctgcggggca    720
gtgctcatcc acccctcctg ggtgctgaca gcggcccact gcatggatga gtccaagaag    780
ctccttgtca ggcttggaga gtatgacctg cggcgctggg agaagtggga gctggacctg    840
gacatcaagg aggtcttcgt ccaccccaac tacagcaaga gcaccagcga caatgacatc    900
gcactgctgc acctggccca gcccgccacc ctctcgcaga ccatagtgcc catctgcctc    960
ccggacagcg gccttgcaga gcgcgagctc aatcaggccg gccaggagac cctcgtgacg   1020
ggctggggct accacagcag ccgagagaag gaggccaaga gaaaccgcac cttcgtcctc   1080
```

-continued

```
aacttcatca agattcccgt ggtcccgcac aatgagtgca gcgaggtcat gagcaacatg    1140
gtgtctgaga acatgctgtg tgcgggcatc ctcggggacc ggcaggatgc ctgcgagggc    1200
gacagtgggg ggcccatggt cgcctccttc cacggcacct ggttcctggt gggcctggtg    1260
agctggggtg agggctgtgg gctccttcac aactacggcg tttacaccaa agtcagccgc    1320
tacctcgact ggatccatgg gcacatcaga gacaaggaag ccccccagaa gagctgggca    1380
ccttag                                                                1386

<210> SEQ ID NO 10
<211> LENGTH: 1386
<212> TYPE: DNA
<213> ORGANISM: Homo sapiens

<400> SEQUENCE: 10
atgtggcagc tcacaagcct cctgctgttc gtggccacct ggggaatttc cggcacacca      60
gctcctcttg actcagtgtt ctccagcagc gagcgtgccc accaggtgct gcggatccgc     120
aaacgtgcca actccttcct ggaggagctc cgtcacagca gcctggagcg ggagtgcata     180
gaggagatct gtgacttcga ggaggccaag gaaattttcc aaaatgtgga tgacacactg     240
gccttctggt ccaagcacgt cgacggtgac cagtgcttgg tcttgccctt ggagcacccg     300
tgcgccagcc tgtgctgcgg gcacggcacg tgcatcgacg gcatcggcag cttcagctgc     360
gactgccgca gcggctggga gggccgcttc tgccagcgcg aggtgagctt cctcaattgc     420
tcgctggaca acggcggctg cacgcattac tgcctagagg aggtgggctg gcggcgctgt     480
agctgtgcgc ctggctacaa gctgggggac gacctcctgc agtgtcaccc cgcagtgaag     540
ttcccttgtg ggaggccctg gaagcggatg gagaagaagc gcagtcacct gaaacgagac     600
acagaagacc aagaagacca agtagatccg cggctcattg atgggaagat gaccaggcgg     660
ggagacagcc cctggcaggt ggtcctgctg gactcaaaga agaaggccgc ctgcggggca     720
gtgctcatcc acccctcctg ggtgctgaca gcggcccact gcatggatga gtccaagaag     780
ctccttgtca ggcttggaga gtatgacctg cggcgctggg agaagtggga gctggacctg     840
gacatcaagg aggtcttcgt ccaccccaac tacagcaaga gcaccagcga caatgacatc     900
gcactgctgc acctggccca gcccgccacc ctctcgcaga ccatagtgcc catctgcctc     960
ccggacagcg gccttgcaga gcgcgagctc aatcaggccg gccaggagac cctcgtgacg    1020
ggctggggct accacagcag ccgagagaag gaggccaaga gaaaccgcac cttcgtcctc    1080
aacttcatca agattcccgt ggtcccgcac aatgagtgca gcgaggtcat gagcaacatg    1140
gtgtctgaga acatgctgtg tgcgggcatc ctcggggacc ggcaggatgc ctgcgagggc    1200
gacagtgggg ggcccatggt cgcctccttc cacggcacct ggttcctggt gggcctggtg    1260
agctggggtg agggctgtgg gctccttcac aactacggcg tttacaccaa agtcagccgc    1320
tacctcgact ggatccatgg gcacatcaga gacaaggaag ccccccagaa gagctgggca    1380
ccttag                                                                1386
```

PROTEIN C DERIVATIVES

Figure 1:
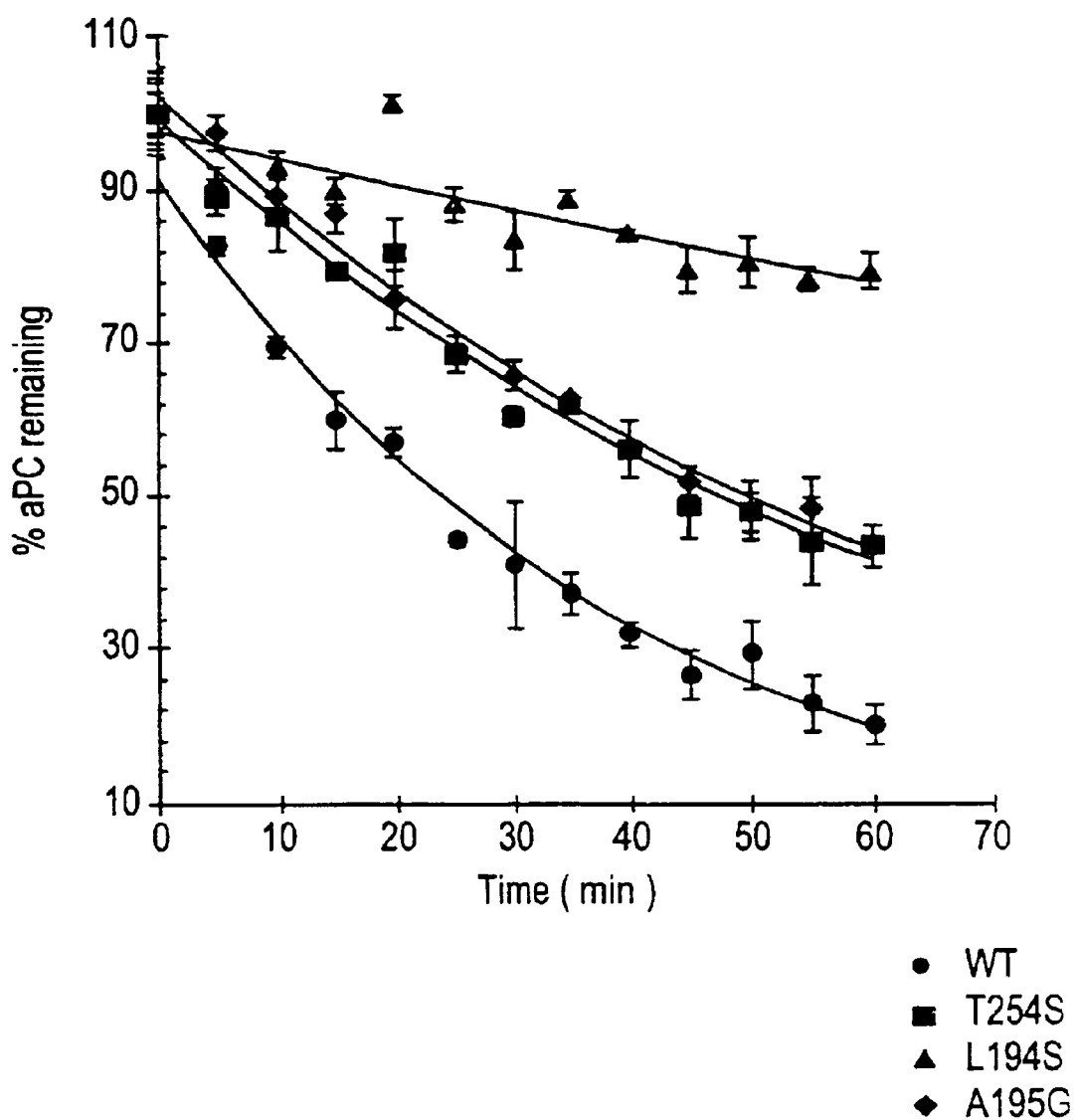

This application claims priority of Provisional Application Ser. No. 60/131,801 filed Apr. 30, 1999.

This invention relates to novel polynucleotides, polypeptides encoded by them and to the use of such polynucleotides and polypeptides. More specifically, the invention relates to protein C derivatives resistant to serpin inactivation, to their production, and to pharmaceutical compositions comprising these protein C derivatives.

Protein C is a serine protease and naturally occurring anticoagulant that plays a role in the regulation of homeostasis by inactivating Factors Va and VIIIa in the coagulation cascade. Human protein C is made in vivo as a single polypeptide of 461 amino acids. This polypeptide undergoes multiple post-translational modifications including 1) cleavage of a 42 amino acid signal sequence; 2) cleavage of lysine and arginine residues (positions 156 and 157) to make a 2-chain inactive precursor or zymogen (a 155 amino acid residue light chain attached via a disulfide bridge to a 262 amino acid residue heavy chain); 3) vitamin K-dependent carboxylation of nine glutamic acid residues of the light chain, resulting in nine gamma-carboxyglutamic acid residues; and 4) carbohydrate attachment at four sites (one in the light chain and three in the heavy chain). Finally, the 2-chain zymogen may be activated by removal of a dodecapeptide at the N-terminus of the heavy chain, producing activated protein C (aPC) possessing greater enzymatic activity than the 2-chain zymogen.

In conjunction with other polypeptides, aPC functions as an anti-coagulant important in protecting against thrombosis, has anti-inflammatory effects through its inhibition of cytokine generation (e.g., TNF and IL-1), and exerts profibrinolytic properties that facilitate clot lysis. Thus, aPC provides a mechanism for anti-coagulation, anti-inflammation, and fibrinolysis.

The critical role of aPC in controlling hemostasis is exemplified by the increased rate of thrombosis in heterozygous deficiency, protein C resistance (e.g., due to the common Factor V Leiden mutation) and the fatal outcome of untreated homozygous protein C deficiency. Plasma-derived and recombinantly produced aPC have been shown to be effective and safe antithrombotic agents in a variety of animal models of both venous and arterial thrombosis.

Protein C levels have also been shown to be abnormally low in the following diseases and conditions: disseminated intravascular coagulation (DIC)[Fourrier, et al., *Chest* 101: 816–823, 1992], sepsis [Gerson, et al., *Pediatrics* 91: 418–422, 1993], major trauma/major surgery [Thomas, et al., *Am J Surg.* 158: 491–494, 1989], burns [Lo, et al., *Burns* 20: 186–187 (1994)], adult respiratory distress syndrome (ARDS)[Hasegawa, et al., *Chest* 105 (1): 268–277, 1994], and transplantations [Gordon, et al., *Bone Marrow Trans.* 11: 61–65 (1993)]. In addition, there are numerous diseases with thrombotic abnormalities or complications that aPC may be useful in treating, such as: heparin-induced thrombocytopenia (HIT) [Phillips, et al., *Annals of Pharmacotherapy* 28: 43–45, 1994], sickle cell disease or thalassemia [Karayalcin, et al., *The American Journal of Pediatric Hematology/Oncology* 11 (3): 320–323, 1989], viral hemorrhagic fever [Lacy, et al., *Advances in Pediatric Infectious Diseases* 12: 21–53, 1997], thrombotic thrombocytopenic purpura (TTP) and hemolytic uremic syndrome (HUS) [Moake, *Seminars in Hematology* 34 (2): 83–89, 1997]. In addition, aPC in combination with Bactericidal Permeability Increasing Protein (BPI) may be useful in the treatment of sepsis [Fisher, et al., *Crit. Care Med.* 22 (4): 553–558, 1994].

Finally, platelet inhibition is efficacious in both prevention and treatment of thrombotic disease. However, the use of antiplatelet agents, such as aspirin, increase the risk of bleeding, which limits the dose of the agent and duration of treatment. The combination of aPC and antiplatelet agents results in a synergy that allows the reduction of the dosages of both aPC and the antiplatelet agent(s). The reduction of the dosages of the agents in combination therapy in turn results in reduced side effects such as increased bleeding often observed in combination anti-coagulant/anti-platelet therapy.

Various methods of obtaining protein C from plasma and producing protein C, aPC and protein C/aPC polypeptides through recombinant DNA technology are known in the art and have been described. See e.g., U.S. Pat. Nos. 4,775,624 and 5,358,932. Despite improvements in methods to produce aPC through recombinant DNA technology, aPC and polypeptides thereof are difficult and costly to produce and have a relatively short half-life in vivo.

A reason for the short half-life is that blood levels of aPC are regulated by molecules known as serpins (Serine Protease Inhibitors), which covalently bind to aPC forming an inactive serpin/aPC complex. The serpin/aPC complexes are formed when aPC binds and proteolytically cleaves a reactive site loop within the serpin; upon cleavage, the serpin undergoes a conformational change irreversibly inactivating aPC. The serpin/aPC complex is then eliminated from the bloodstream via hepatic receptors for the serpin/aPC complex. As a result, aPC has a relatively short half-life compared to the zymogen; approximately 20 minutes for aPC versus approximately 10 hours for human protein C zymogen (Okajima, et al., *Thromb Haemost* 63 (1): 48–53, 1990).

It has been shown that changes to serine protease amino acid sequences at residues which interact directly with the substrate (generally within or near the active site) can alter the specificity of the serine protease, potentially providing increased specific activity towards appropriate coagulation factors, as well as increased resistance to serpins (Rezaie, *J Biol Chem* 271 (39): 23807–23814, 1996; Rezaie and Esmon, *Eur. J. Biochem* 242: 477–484, 1996). Therefore, an aPC polypeptide exhibiting increased resistance to serpin inactivation, while maintaining the desirable biological activities of aPC (e.g., anti-coagulant, fibrinolytic, and anti-inflammatory activities), provides a compound that has an increased plasma half-life and, therefore, is effectively more potent than the parent compound, requiring substantially reduced dosage levels or less frequent administrations for therapeutic applications. The potency advantages are especially important in disease states in which serpin levels are elevated.

Physiologically, the two serpins that serve as the primary inactivators of aPC are protein C inhibitor (PCI) and $\alpha_1$-antitrypsin ($\alpha_1$-AT) [Heeb, et al., *J Biol Chem* 263 (24): 11613–6, 1988]. Both PCI and $\alpha_1$-AT have been demonstrated to be the primary physiological inactivators of aPC in disease states such as disseminated intravascular coagulation (Scully, et al., *Thromb Haemost* 69 (5): 448–53, 1993), and elevated levels of $\alpha_1$-AT have been observed in a number of disease states involving an inflammatory response (Somayajulu, et al., *J Pathol Microbiol* 39 (4): 271–5, 1996;

Morgan, et al., *Int J Biochem Cell Biol* 29 (12): 1501–11, 1997). The elevated serpin levels inactivate aPC resulting in an increased susceptibility of coagulapathies associated with decreased protein C levels. Attempts have been made to increase the plasma half-life of aPC by increasing the resistance to serpins by modifying the human protein C molecule (e.g., U.S. Pat. No. 5,358, 932). An increase in immunogenicity is often observed when a natural protein is significantly modified and then administered to a patient.

Through scientific experiment and analysis, we identified serpin and protein C binding sites essential to formation of serpin/aPC complexes. We modified targeted amino acid residues in the aPC molecule and surprisingly found that we were able to inhibit formation of the serpin/aPC complex (the complex which irreversibly inactivates aPC) while at the same time retaining the specificity of the aPC polypeptide for aPC's natural substrates (e.g. factor Va and VIIIa). In particular, three sites of recognition within the aPC active site show distinctive differences between substrate recognition sequences and inhibitor recognition sequences: S2, S3', and S4'. We found inhibition of serpin/human aPC polypeptide binding by substituting one or more of the following amino acids: 194 (Leu), 195 (Ala), 228 (Leu), 249 (Tyr), 254 (Thr), 302 (Tyr), and 316 (Phe) of SEQ ID NO: 7 with an amino acid(s) selected from Ser, Ala, Thr, His, Lys, Arg, Asn, Asp, Glu, Gly, and Gln, provided that 195 is not substituted with Ala and 254 is not substituted with Thr.

Accordingly, the present invention describes novel protein C derivatives. These protein C derivatives retain the important biological activity of the wild-type protein C (SEQ ID NO: 2.) and have substantially longer half-lives in human blood. Therefore, these compounds provide various advantages, eg. less frequent administration and/or smaller dosages and thus a reduction in the overall cost of production of the therapy. Additionally, these compounds exhibit an advantage in disease states with significantly elevated $\alpha_1$-AT levels such as sepsis. Importantly, the increases in protein C derivative plasma half-lives may be achieved via single amino acid substitutions, which are less likely to be immunogenic in comparison to molecules which contain multiple amino acid substitutions (U.S. Pat. No. 5,358,932; Holly, et al., *Biochemistry* 33: 1876–1880, 1994).

The present invention provides a protein C derivative comprising SEQ ID NO: 1 and the corresponding amino acids in SEQ ID NO: 2, wherein one or more of amino acids 194, 195, 228, 249, 254, 302, or 316 is substituted with an amino acid selected from Ser, Ala, Thr, His, Lys, Arg, Asn, Asp, Glu, Gly, and Gln, provided that amino acid 195 is not Ala and amino acid 254 is not Thr. The invention further provides the activated form of the above-identified protein C derivatives.

The present invention also provides recombinant DNA molecules encoding the protein C derivatives in the preceding paragraph, in particular those comprising SEQ ID NOS: 8, 9, and 10.

Another aspect of the present invention provides protein sequences of these same protein C derivatives, particularly those comprising SEQ ID NOS: 3, 4, and 5 and the activated forms of these protein C derivatives.

The present invention comprises methods of treating vascular occlusive disorders and hypercoagulable states including: sepsis, disseminated intravascular coagulation, purpura fulminans, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome. The invention further provides treating these same diseases and conditions employing the activated form of the above-identified protein C derivatives.

Another embodiment of the present invention is a method of treating sepsis comprising the administration to a patient in need thereof a pharmaceutically effective amount of a protein C derivative of this invention in combination with bacterial permeability increasing protein.

The present invention comprises methods of treating acute coronary syndromes such as myocardial infarction and unstable angina.

The present invention further comprises methods of treating thrombotic disorders. Such disorders include, but are not limited to, stroke, abrupt closure following angioplasty or stent placement, and thrombosis as a result of peripheral vascular surgery.

The present invention also provides a pharmaceutical composition comprising a protein C derivative of this invention.

Human protein C derivatives for the above-mentioned indications and pharmaceutical compositions are preferably selected from L194S, L194S:T254S, and L194A:T254S.

Methods and aspects of producing the novel isolated human protein polypeptides are also an aspect of this invention.

Finally, an aspect of the invention comprises treating the diseases and conditions caused or resulting from protein C deficiency as defined herein, by inhibiting binding to inhibitor recognition sequences S2, S3', and S4' of the serpins, PCI and $\alpha_1$-AT. This final aspect of the invention contemplates any and all modifications to any aPC molecule resulting in inhibition of the binding to said inhibitor recognition sequences of the serpins PCI and $\alpha_1$-AT. The inhibition of binding to the specific inhibitor recognition sequences of the serpins (S2, S3', and S4') being an important contribution to this aspect of the invention.

FIG. 1. Inactivation of human aPC polypeptides during incubation with normal human plasma. Remaining activity is measured as amidolytic activity normalized to activity at the start of the experiment (time=0); error bars indicate the standard error of triplicate experiments. Data are shown for the wild-type protein C (WT, circles), T254S (squares), L194S (triangles), and A195G (diamonds).

FIG. 2. Inactivation of human aPC polypeptides during incubation with normal human plasma. Remaining activity is measured as amidolytic activity normalized to activity at the start of the experiment (time=0); error bars indicate the standard error of triplicate experiments. Data are shown for the wild-type protein C (WT, circles), L194A/T254S (squares), and L194S/T254S (triangles).

FIG. 3. Inactivation of human aPC polypeptides by normal human plasma containing Heparin (10 U/mL). Remaining activity is measured as amidolytic activity normalized to activity at the start of the experiment (time=0) error bars indicate the standard error of triplicate experiments. Data are shown for the wild-type protein C(WT, circles), T254S (squares), L194S (triangles), and A195G (diamonds).

FIG. 4. Inactivation of human aPC polypeptides by purified $\alpha_1$-antitrypsin. Remaining activity is measured as amidolytic activity normalized to activity at the start of the experiment (time=0); error bars indicate the standard error of triplicate experiments. Data are shown for the wild-type protein (WT, circles), T254S (squares), L194S (triangles), and A195G (diamonds).

FIG. 5. Plasma aPC levels following a bolus IV dose of 0.1 mg/kg in normal, conscious rabbits (N=3). Activated protein C levels were determined using immunocapture assay, and compared to a standard curve generated from dilutions of the purified protein in rabbit plasma; the standard curve ranged from 1 to 250 ng/mL, with the calculated values within 10% of the standard samples. Data are shown for the wild-type protein (WT, circles), T254S (squares), L194S (triangles), and L194S/T254S (diamonds). The values plotted are the mean and standard error for the three animals.

For purposes of the present invention, as disclosed and claimed herein, the following terms are as defined below.

Antiplatelet agent—one or more agents alone or in combination which reduces the ability of platelets to aggregate. Agents understood and appreciated in the art include those cited in, for example, Remington, *The Science and Practice of Pharmacy*, Nineteenth Edition, Vol II, pages 924–25, Mack Publishing Co., herein incorporated by reference. Such agents include but are not limited to aspirin (ASA), clopidogrel, ReoPro® (abciximab), dipyridamole, ticlopidine and IIb/IIIa antagonists.

aPC or activated protein C refers to recombinant aPC. aPC includes and is preferably recombinant human aPC although aPC may also include other species having protein C proteolytic, amidolytic, esterolytic, and biological (anticoagulant, anti-inflammatory, or pro-fibrinolytic) activities.

Protein C derivative(s) refers to the recombinantly produced polypeptides of this invention that differ from wild-type human protein C but when activated retain the essential properties i.e., proteolytic, amidolytic, esterolytic, and biological (anti-coagulant, anti-inflammatory, pro-fibrinolytic activities). The definition of protein C derivatives as used herein also includes the activated form of the above identified protein C derivatives.

Treating—describes the management and care of a patient for the purpose of combating a disease, condition, or disorder whether to eliminate the disease, condition, or disorder, or prophylactically to prevent the onset of the symptoms or complications of the disease, condition, or disorder.

Continuous infusion continuing substantially uninterrupted the introduction of a solution or suspension into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Unit dosage form—refers to physically discrete units suitable as unitary dosages for human subjects, each unit containing a predetermined quantity of active material calculated to produce the desired therapeutic effect, in association with a suitable pharmaceutical excipient.

Hypercoagulable states—excessive coagulability associated with disseminated intravascular coagulation, pre-thrombotic conditions, activation of coagulation, or congenital or acquired deficiency of clotting factors such as aPC.

Zymogen—protein C zymogen, as used herein, refers to secreted, inactive forms, whether one chain or two chains, of protein C.

Pharmaceutically effective amount—a therapeutically efficacious amount of a pharmaceutical compound. The particular dose of the compound administered according to this invention will, of course, be determined by the attending physician evaluating the particular circumstances surrounding the case, including the compound administered, the particular condition being treated, the patient characteristics and similar considerations.

Acute coronary syndromes—clinical manifestations of coronary atherosclerosis complicated by coronary plaque rupture, superimposed coronary thrombosis, and jeopardized coronary blood flow resulting in coronary ischemia and/or myocardial infarction. The spectrum of acute coronary syndromes includes unstable angina, non-Q-wave (i.e., non-ST-segment elevation) myocardial infarction, and Q-wave (i.e., ST-segment elevation) myocardial infarction.

Thrombotic disorders—a disorder relating to, or affected with the formation or presence of a blood clot within a blood vessel. Such disorders include, but are not limited to, stroke, abrupt closure following angioplasty or stent placement, and thrombosis as a result of peripheral vascular surgery.

Purpura fulminans—ecchymotic skin lesions, fever, hypotension associated with bacterial sepsis, viral, bacterial or protozoan infections. Disseminated intravascular coagulation is usually present.

Serpin—any of a group of structurally related proteins that typically are serine protease inhibitors whose inhibiting activity is conferred by an active site in a highly variable and mobile peptide loop and that include but are not limited to protein C inhibitor (PCI) and a antitrypsin ($\alpha_1$-AT).

Inhibitor recognition sequence S2: the $2^{nd}$ residue N-terminal to the cleavage site of PCI or $\alpha_1$-AT.

Inhibitor recognition sequence S3': the $3^{rd}$ residue C-terminal to the cleavage site of PCI or $\alpha_1$-AT.

Inhibitor recognition sequence S4': the $4^{th}$ residue C-terminal to the cleavage site of PCI or $\alpha_1$-AT.

Wild-type protein C—the type of protein C that predominates in a natural population of humans in contrast to that of natural or laboratory mutant or polypeptide forms of protein C.

Bactericidal permeability increasing protein—includes naturally and recombinantly produced bactericidal permeability increasing (BPI) protein; natural, synthetic, and recombinant biologically active polypeptide fragments of BPI protein; biologically active polypeptide variants of BPI protein or fragments thereof, including hybrid fusion proteins and dimers; biologically active variant analogs of BPI protein or fragments or variants thereof, including cysteine-substituted analogs; and BPI-derived peptides. The complete amino acid sequence of human BPI, as well as the nucleotide sequence of DNA encoding BPI have been elucidated by Gray, et al., 1989, *J. Biol. Chem* 264:9505. Recombinant genes encoding and methods for expression of BPI proteins, including BPI holoprotein and fragments of BPI are disclosed in U.S. Pat. No. 5,198,541, herein incorporated by reference.

The amino acid abbreviations are accepted by the United States Patent and Trademark Office as set forth in 37 C.F.R. 1.822 (d)(1) (1998).

The activated form of aPC or isolated human aPC polypeptides may be produced by activating recombinant human protein C zymogen or recombinant protein C derivative zymogen in vitro or by direct secretion of the activated form of protein C. The means by which the activation occurs is not critical and the process aspects of this invention include any and all means of activation. Protein C derivatives may be produced in eukaryotic cells, transgenic animals, or transgenic plants, including, for example, secretion from human kidney 293 cells as a zymogen then purified and activated by techniques known to the skilled artisan.

The present invention provides protein C derivatives, including activated forms thereof, which have increased resistance to serpins, and consequently result in extended plasma half-lives. Specific protein C derivatives include L194S, L194S:T254S, and L194A:T254S and activated forms thereof.

Figure 4:
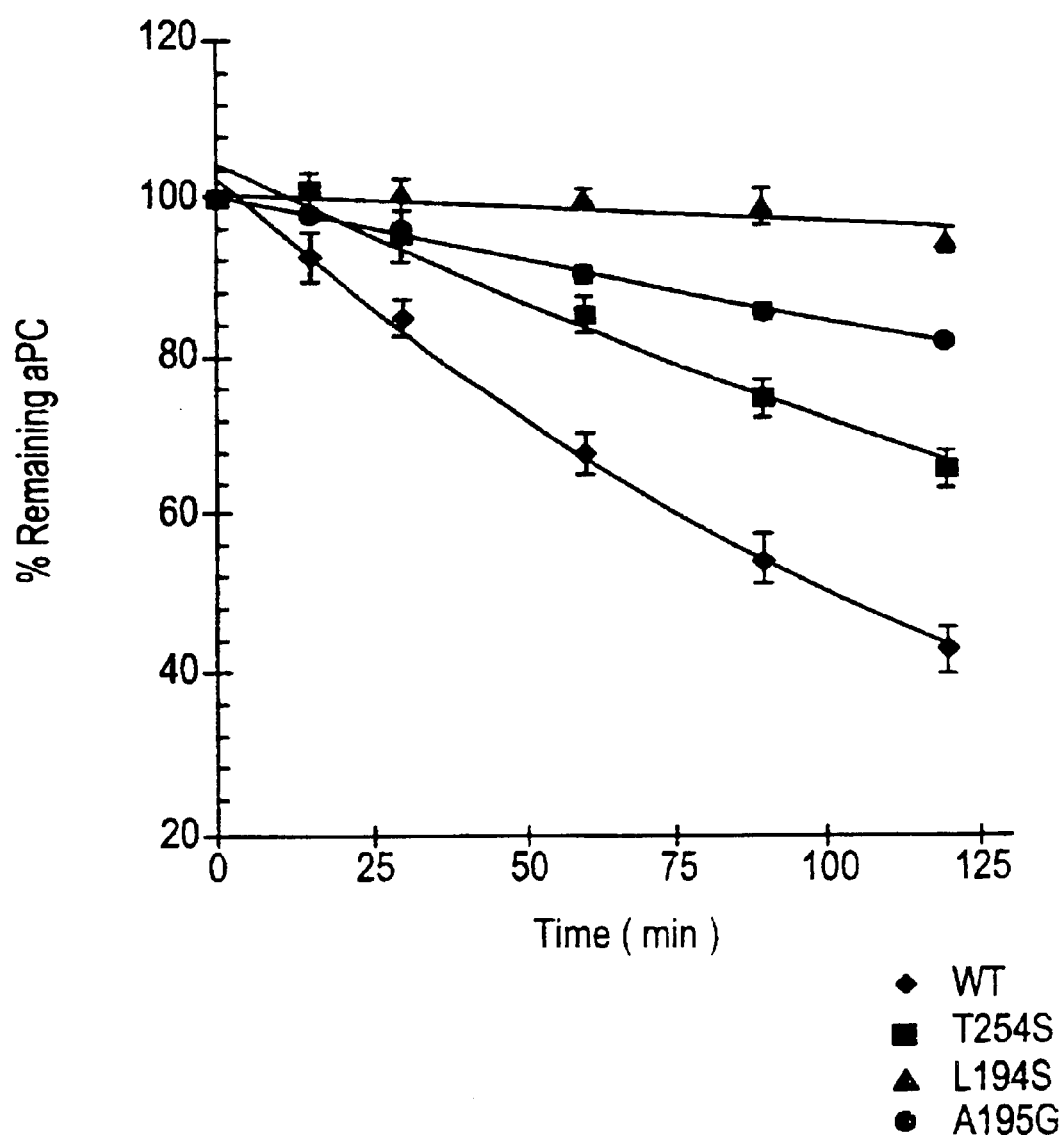

Protein C derivative L194S preferably contains a serine residue at position 194 rather than a leucine residue normally found at this position. One with skill in the art would realize that other amino acid substitutions at residue 194 in addition to Ser may impart increased resistance to serpins in the resulting polypeptide molecule. Examples of such amino acid substitutions include, Ala, Thr, His, Lys, Arg, Asn, Asp, Glu, and Gln. The activated form of protein C derivative L194S demonstrates prolonged half-life in plasma (FIG. 1) and increased resistance to serpins, for example, $\alpha_1$-antitrypsin ($\alpha_1$-AT), FIG. 4.

Figure 2:
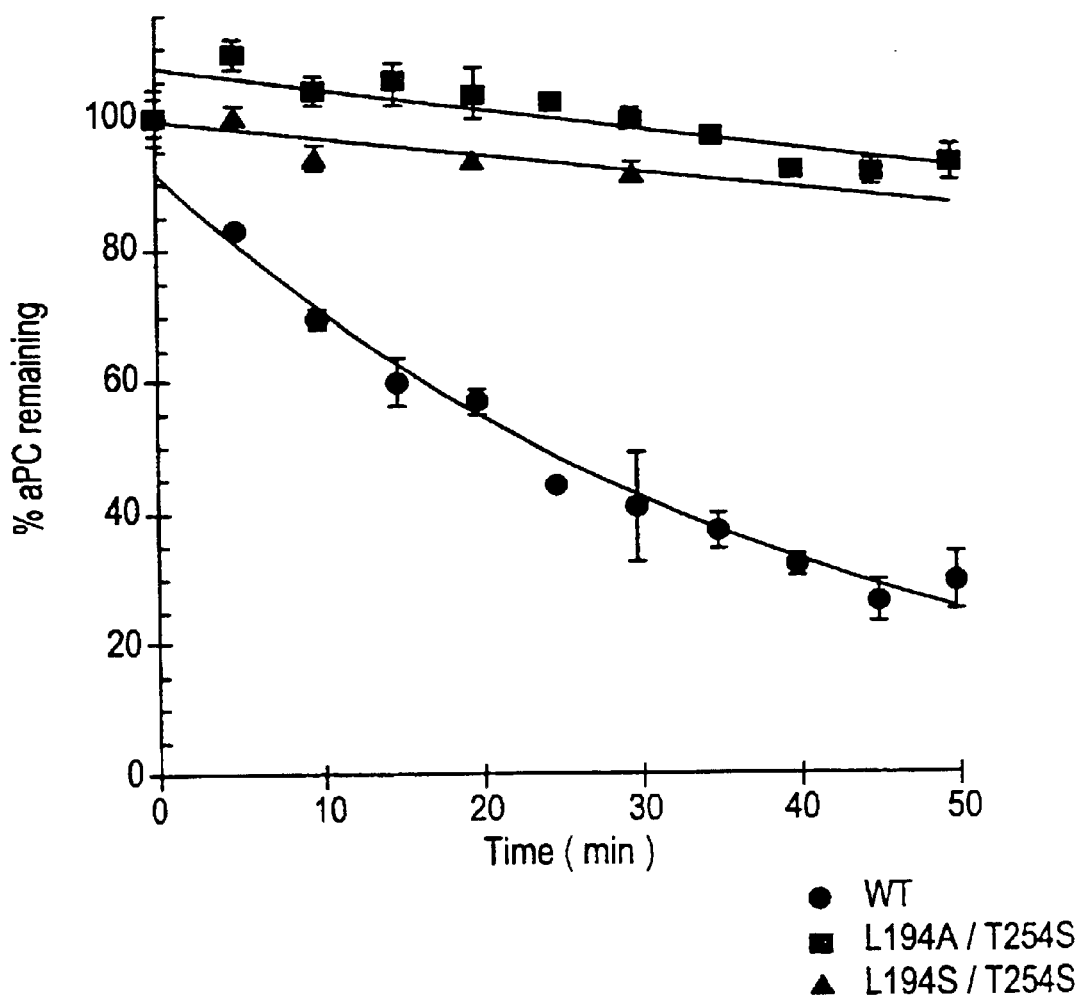

Protein C derivative L194S:T254S preferably contains a serine residue at position 194 rather than a leucine residue normally found at this position and a serine residue at position 254 rather than a threonine residue normally found at this position. It is apparent to one with skill in the art that other amino acid substitutions at residues 194 and 254 in addition to Ser may impart increased resistance to serpins in the resulting polypeptide molecule. Examples of such amino acid substitutions include Ala, Thr, His, Lys, Arg, Asn, Asp, Glu, Gln, and Gly, provided that amino acid 254 is not substituted with Thr. The activated form of human protein C derivative L194S:T254S demonstrates a prolonged half-life in normal human plasma compared to wild-type protein C, FIG. 2.

Protein C derivative L194A:T254S preferably contains an alanine residue at position 194 rather than a leucine residue normally found at this position and a serine residue at position 254 rather than a threonine residue normally found at this position. It is apparent to one with skill in the art that other amino acid substitutions at residues 194 and 254 in addition to Ser may impart increased resistance to serpins in the resulting polypeptide molecule. Examples of such amino acid substitutions include Ala, Thr, His, Lys, Arg, Asn, Asp, Glu, Gln, and Gly, provided that amino acid 254 is not substituted with Thr. The activated form of human protein C derivative L194A:T254S demonstrates a prolonged half-life in normal human plasma compared to wild-type protein C, FIG. 2.

Further embodiments of the present invention include protein C derivatives: L194T, L194A, A195G, L228Q, T254S, F316N, Y249E, and Y302Q, and activated forms thereof which have increased resistance to serpins.

Protein C derivatives L194T or L194A preferably contain a threonine residue or an alanine residue at position 194 rather than a leucine residue normally found at this position. One with skill in the art would realize that other amino acid substitutions at residue 194 in addition to Ser may impart increased resistance to serpins in the resulting polypeptide molecule. Examples of such amino acid substitutions include, His, Lys, Arg, Asn, Asp, Glu, and Gln.

Protein C derivative A195G preferably contains a glycine residue at position 195 rather than an alanine residue normally found at this position. One with skill in the art would realize that other amino acid substitutions at residue 195 in addition to Gly may impart increased resistance to serpins in the resulting polypeptide molecule. Examples of such amino acid substitutions include Ser, Ala, Thr, His, Lys, Arg, Asn, Asp, Glu, and, Gln. The activated form of protein C derivative A195G demonstrates prolonged half-life in plasma (FIG. 1) and increased resistance to serpins, for example, $\alpha_1$-antitrypsin ($\alpha_1$-AT), FIG. 4.

Protein C derivative L228Q preferably contains a glutamine residue at position 228 rather than a leucine residue normally found at this position. One with skill in the art would realize that other amino acid substitutions at residue 228 in addition to Gln may impart increased resistance to serpins in the resulting polypeptide molecule. Examples of such amino acid substitutions include, Ser, Ala, Thr, His, Lys, Arg, Asn, Asp, Glu, and Gly.

Protein C derivative T254S preferably contains a serine residue at position 254 rather than a threonine residue normally found at this position. It is apparent to one with skill in the art that other amino acid substitutions at residue 254 in addition to Ser may impart increased resistance to serpins in the resulting polypeptide molecule. Examples of such amino acid substitutions include Ala, Thr, His, Lys, Arg, Asn, Asp, Glu, Gln, and Gly, provided that amino acid 254 is not substituted with Thr. The activated form of protein C derivative T254S demonstrates prolonged half-life in plasma (FIG. 1) and increased resistance to serpins, for example, $\alpha_1$-antitrypsin ($\alpha_1$-AT), FIG. 4.

Protein C derivative F316N preferably contains an asparagine residue at position 316 rather than a phenylalanine residue normally found at this position. One with skill in the art would realize that other amino acid substitutions at residue 316 in addition to Asn may impart increased resistance to serpins in the resulting polypeptide molecule. Examples of such amino acid substitutions include, Ser, Ala, Thr, His, Lys, Arg, Asp, Glu, Gln, and Gly.

Protein C derivative Y249E preferably contains a glutamic acid residue at position 249 rather than a tyrosine residue normally found at this position. An additional polypeptide contains an Asp at position 249 rather than a tyrosine residue. One with skill in the art would realize that other amino acid substitutions at residue 249 in addition to Glu and Asp may impart increased resistance to serpins in the resulting polypeptide molecule. Examples of such amino acid substitutions include, Ser, Ala, Thr, His, Lys, Arg, Asn, Gln, and Gly.

Protein C derivative Y302Q preferably contains a glutamine residue at position 302 rather than a tyrosine residue normally found at this position. An additional polypeptide contains a Glu at position 302 rather than a tyrosine residue. One with skill in the art would realize that other amino acid substitutions at residue 302 in addition to Glu or Gln may impart increased resistance to serpins in the resulting polypeptide molecule. Examples of such amino acid substitutions include, Ser, Ala, Thr, His, Lys, Arg, Asn, Asp, and Gly.

In addition, protein C derivatives may include proteins that represent functionally equivalent gene products. Such an equivalent protein C derivative may contain deletions, additions, or substitutions of amino acid residues within the amino acid sequence encoded by the protein C polypeptide gene sequences described above, but which result in a silent change, thus producing a functionally equivalent protein C derivative gene product. Amino acid substitutions may be made on the basis of similarity in polarity, charge, solubility, hydrophobicity, hydrophilicity, and/or the amphipathic nature of the residues involved.

Thus, the polypeptides of the present invention include polypeptides having an amino acid sequence at least identical to that of SEQ ID NOS: 3, 4, or 5, or fragments thereof with at least 90% identity to the corresponding fragment of SEQ ID NOS: 3, 4, or 5. Preferably, all of these polypeptides retain the biological activity of human aPC. Preferred polypeptides are those that vary from SEQ ID NOS: 3, 4, or 5 by conservative substitutions i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are polypeptides in which several, 5–10, 1–5, or 1–2 amino acids are substituted, deleted, or added in any combination.

The invention also provides DNA compounds for use in making the protein C derivatives. These DNA compounds comprise the coding sequence for the light chain of human protein C zymogen or protein C derivative zymogen positioned immediately adjacent to, downstream of, and in translational reading frame with the prepropeptide sequence of human protein C zymogen or protein C derivative zymogen. The DNA sequences preferably encode the Lys-Arg dipeptide which is processed during maturation of the protein C molecule, the activation peptide and the heavy chain of the protein C derivative.

Those skilled in the art will recognize that, due to the degeneracy of the genetic code, a variety of DNA compounds can encode the polypeptides described above. U.S. Pat. No. 4,775,624, the entire teaching of which is herein incorporated by reference, discloses the wild-type form of the human protein C molecule. The skilled artisan could readily determine which changes in the DNA sequences which could encode the exact polypeptides as disclosed herein.

The invention is not limited to the specific DNA sequences disclosed. Consequently, the construction described below and in the accompanying Examples for the preferred DNA compounds are merely illustrative and do not limit the scope of the invention.

All of the DNA compounds of the present invention were prepared by the use of site-directed mutagenesis to change particular positions within human protein C zymogen. The methods used for the identification of residues which form critical contacts in these particular positions are described in Example 1.

The protein C derivatives can be made by techniques well known in the art utilizing eukaryotic cell lines, transgenic animals, or transgenic plants. Skilled artisans will readily understand that appropriate host eukaryotic cell lines include but are not limited to HepG2, LLC-MK$_2$, CHO-K1, 293, or AV12 cells, examples of which are described in U.S. Pat. No. 5,681,932, herein incorporated by reference. Furthermore, examples of transgenic production of recombinant proteins are described in U.S. Pat. Nos. 5,589,604 and 5,650,503, herein incorporated by reference.

Skilled artisans recognize that a variety of vectors are useful in the expression of a DNA sequence of interest in a eukaryotic host cell. Vectors that are suitable for expression in mammalian cells include, but are not limited to; pGT-h, pGT-d; pcDNA 3.0, pcDNA 3.1, pcDNA 3.1+Zeo, and pcDNA 3.1+Hygro (Invitrogen); and, pIRES/Hygro, and pIRES/neo (Clonetech). The preferred vector of the present invention is pIG3 as described in Example 2.

To be fully active and operable under the present methods, the protein C derivatives made by any of these methods must undergo post-translational modifications such as the addition of nine gamma-carboxy-glutamates, the addition of one erythro-beta-hydroxy-Asp (beta-hydroxylation), the addition of four Asn-linked oligosaccharides (glycosylation) and, the removal of the leader sequence (42 amino acid residues). Without such post-translational modifications, the protein C polypeptides are not fully functional or are non-functional.

Methods for the activation of zymogen forms of human protein C and protein C derivatives to activated human protein C and activated protein C derivatives are old and well known in the art. Human protein C may be activated by thrombin alone, by a thrombin/thrombomodulin complex, by Rvv-X, a protease from Russell's Viper venom, by pancreatic trypsin or by other proteolytic enzymes.

The recombinant protein C derivatives of the present invention are useful for the treatment of vascular occlusive disorders or hypercoagulable states associated with sepsis, disseminated intravascular coagulation, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome. In another embodiment, the recombinant protein C derivatives of the present invention are useful for the treatment of sepsis in combination with bacterial permeability increasing protein. In yet another aspect of this invention the activated protein C derivatives of the present invention are combined with an antiplatelet agent(s) to treat or prevent various disorders, such as, thrombotic disease.

The present invention further provides for the treatment of acute coronary syndromes comprising myocardial infarction, and unstable angina with human protein C derivatives with resistance to serpin inactivation as compared to wild-type aPC.

The recombinant human protein C derivatives of the present invention are also useful for the treatment of thrombotic disorders such as stroke, abrupt closure following angioplasty or stent placement, and thrombosis as a result of peripheral vascular surgery.

The protein C derivatives can be formulated according to known methods to prepare a pharmaceutical composition comprising as the active agent an aPC polypeptide and a pharmaceutically acceptable solid or carrier. For example, a desired formulation would be one that is a stable lyophilized product of high purity comprising a bulking agent such as sucrose, a salt such as sodium chloride, a buffer such as sodium citrate and an activated protein C derivative. A preferred stable lyophilized formulation comprises: 2.5 mg/ml activated protein C polypeptide, 15 mg/ml sucrose, 20 mg/ml NaCl and a citrate buffer, said formulation having a pH of 6.0. An additional stable lyophilized formulation comprises: 5.0 mg/ml activated protein C polypeptide, 30 mg/ml sucrose, 38 mg/ml NaCl and a citrate buffer, said formulation having a pH of 6.0.

Preferably, the human aPC polypeptides will be administered parenterally to ensure delivery into the bloodstream in an effective form by injecting the appropriate dose as a continuous infusion for 1 to 240 hours. More preferably, the human aPC polypeptides will be administered as a continuous infusion for 1 to 192 hours.

Even more preferably, the human aPC polypeptides will be administered as a continuous infusion for 1 to 144 hours. Yet even more preferably, the aPC polypeptides will be administered as a continuous infusion for 1 to 96 hours.

The amount of human aPC polypeptide administered will be from about 0.01 μg/kg/hr to about 50 μg/kg/hr. More preferably, the amount of human aPC polypeptide administered will be about 0.1 μg/kg/hr to about 25 μg/kg/hr. Even more preferably the amount of human aPC polypeptide administered will be about 1 μg/kg/hr to about 15 μg/kg/hr. The most preferable amounts of human aPC polypeptide administered will be about 5 μg/kg/hr or about 10 μg/kg/hr.

Alternatively, the human aPC polypeptide will be administered by injecting a portion (⅓ to ½) of the appropriate dose per hour as a bolus injection over a time from about 5 minutes to about 120 minutes, followed by continuous infusion of the appropriate dose for up to 240 hours.

In another alternative the human aPC derivatives will be administered by injecting a dose of 0.01 mg/kg/day to about 1.0 mg/kg/day, B.I.D. (2 times a day), for one to ten days. More preferably, the human aPC derivatives will be administered B.I.D. for three days.

In yet another alternative, the human aPC polypeptides will be administered subcutaneously to ensure a slower release into the bloodstream. Formulation for subcutaneous preparations will be done using known methods to prepare such pharmaceutical compositions.

An additional aspect of the invention comprises treating the diseases and conditions caused or resulting from protein C deficiency as defined herein, by inhibiting binding to inhibitor recognition sequences S2, S3', and S4' of the serpins, PCI and $\alpha_1$-AT, as described in Example 1.

This final aspect of the invention contemplates any and all modifications to any aPC molecule resulting in inhibition of the binding to said inhibitor recognition sequences of the serpins PCI and $\alpha_1$-AT.

The human aPC polypeptides described in this invention have essentially the same type of biological activity as the wild-type human aPC, with substantially longer half-lives in human blood. Therefore, these compounds will require either less frequent administration and/or smaller dosage. Additionally, these compounds will exhibit an advantage in disease states with significantly elevated $\alpha_1$-AT levels such as sepsis. Finally, superior increases in human aPC polypeptide plasma half-lives may be achieved via one or two amino acid substitutions, which are less likely to be immunogenic compared to greater numbers of substitutions.

The following Examples are provided merely to further illustrate the present invention. The scope of the invention shall not be construed as merely consisting of the following Examples.

EXAMPLE 1

Site-Directed Mutagenesis

The use of site-directed mutagenesis to change particular positions within human protein C molecule that decrease inactivation by serpins, and consequently result in extended plasma half-lives is described. The recognition sequences in the two primary aPC inhibitors $\alpha_1$-AT and PCI reveal some differences that can be exploited by altering the residues in aPC that interact with these sequences. Table I depicts the sequences recognized by aPC. The cleavage site occurs between the two residues shown in italics. Residues occupying the specific subsites, S2, S3', and S4', are underlined.

In general, the recognized sites in factor Va are different from the sites in either factor VIIIa or the inhibitors, therefore, it is possible to engineer the active site of aPC to preferentially cleave the more critical coagulant factor Va, while at the same time decrease aPC's likelihood of being inhibited by serpins.

In particular, three sites of recognition within the active site show distinctive differences between substrate recognition sequences and inhibitor recognition sequences: S2 (the $2^{nd}$ residue N-terminal to the cleavage site), S3' site, and S4'. The S2 site is primarily occupied by polar residues in the factor Va sequences; unlike PCI and $\alpha_1$-AT, which have hydrophobic residues at this position. The S3' site occupied by polar side chains in all of the substrate sequences, but notably, a hydrophobic side chain in the $\alpha_1$-AT sequence. The S4' site is occupied by charged residues in all three factor Va sequences, but is occupied by hydrophobic residues in the factor VIIIa and inhibitor sequences.

Based upon the crystal structures of the PPACK-inhibited aPC (Mather, et al., *EMBO J.* 15 (24): 6822–6831, 1996) and Hirulog 3-inhibited thrombin (Qiu, et al., *Biochemistry* 31 (47): 11689–97, 1992), two aPC-substrate model structures were created and energy minimized using a CHARMm protocol:

(1) The sequence representing the factor Va R506 cleavage sequence.
(2) The recognition sequence of $\alpha_1$-AT, with the Met substituted with Arg (corresponding to a polypeptide of $\alpha_1$-AT which exhibits extremely high affinity for aPC).

These models allowed for the identification of residues which form critical contacts in these three specific sites. A summary of residues which may form specific contacts within the active site, and replacements that are expected to provide enhanced specificity and/or activity are summarized in Table II. In general, mutations of residues that form contacts within the specific subsites of the active site are designed to reflect changes in the environment to drive the specificity of human aPC polypeptides away from the recognition of the two primary physiological inhibitors, and potentially enhance human aPC polypeptide's proteolytic activity.

TABLE II

Mutations constructed for alteration of specificity

| Site | aPC Residue | Constructed replacements | Substrate Contact |
|---|---|---|---|
| S2 | Thr254 | Ser | Aliphatic part of sidechain |
| S3' | Tyr302 | Glu, Gln | End of sidechain |
| S4' | Leu194 | Ser, Thr, Ala | Aliphatic part of sidechain |
| S4' | Ala195 | Gly | Aliphatic part of sidechain |
| S4' | Leu228 | Gln | End of sidechain |
| S4' | Phe316 | Asn | Aliphatic part of sidechain |

EXAMPLE 2

Protein C Polypeptide Construction and Production

Protein C derivatives were constructed using the polymerase chain reaction (PCR) following standard methods. The source of the wild-type coding sequence was plasmid pLPC (Bio/Technology 5:1189–1192, 1987). The universal PCR primers used include: PC001b; 5'-GCGATG TCTAGAccaccATGTGGCAGCTCACAAGCCTCCTGC-3', which encodes for an XbaI restriction site (underlined) used

TABLE I

| Coagulation Factors | | | | | | | S2 | | | | S3' | S4' | | | |
|---|---|---|---|---|---|---|---|---|---|---|---|---|---|---|---|
| Factor Va | 300–313 | N | C | P | K | K | T | *R* | *N* | L | K | K | I | T | R |
| Factor Va | 500–513 | S | R | S | L | D | R | *R* | *G* | I | Q | R | A | A | A |
| Factor Va | 673–685 | S | T | V | M | A | T | *R* | *K* | M | H | D | R | L | E |
| Factor VIIIa | 330–341 | P | E | E | P | Q | L | *R* | *M* | K | N | N | E | E | A |
| Factor VIIIa | 560–571 | K | E | S | V | D | Q | *R* | *G* | N | Q | I | M | S | D |
| Serpins | | | | | | | | | | | | | | | |
| PCI | | G | T | I | F | T | F | *R* | *S* | A | R | L | N | S | Q |
| $\alpha_1$-AT | | F | L | E | A | I | P | *M* | *S* | I | P | P | E | V | K | for subcloning, a Kozak consensus sequence (lowercase) (Kozak, *J Cell Biol* 108 (2): 229–41, 1989), and the 5' end of the coding region for protein C: PC002E; 5'-CAGGGA TGATCACTAAGGTGCCCAGCTCTTCTGG-3', which encodes for the 3' end of the coding region for human protein C, and includes a BclI restriction site (underlined) for subcloning. Mutagenic PCR primers (sense and anti-sense directions, respectively) include: PC194SF, 5'-CTCAAAGAAGAAGTCCGCCTGCGGGGCAGTGC-3' and PC194SR, 5'-GCACTGCCCCGCAGGCGGACTT-CTTCTTTGAG-3' which encode for a Leu (CTG) to Ser (TCC) mutation at position 194 (boldfaced type); PCA195GF, 5'-GAAGAAGCTGGGGTGCGGGGCAGTG-C-3', and PCA195GR, 5'-GCACTGCCCCGCACCCCAG-CTTCTTC-3', which encode for a Ala(GCC) to Gly(GGG) mutation; PCT254SF, 5'-GCAAGAGCACCAGCGACAAT-GAC-ATCGC-3' and PCT254SR, 5'-GCGATGTCATTGT-CGCTGGTGCTCTTGC-3', which encode for a Thr (ACC) to Ser (AGC) mutation at position 254 (boldfaced type). The first round of PCR was used to amplify two fragments of the protein C gene; the 5' fragment was generated using PC001b and the antisense mutagenic primer, and the 3' fragment was generated using PC002e and the sense mutagenic primer. The resulting amplified products were purified by standard procedures. These fragments were combined and then used as a template for a second round of PCR using primers PC001b and PC002e. The final PCR product was digested with XbaI and BclI and subcloned into similarly digested expression vector pIG3. A wild-type construct was similarly generated by PCR using the two universal primers and the plasmid pLPC as the template, followed by subcloning into pIG3. The mutations were confirmed by DNA sequencing of both the coding and non-coding strands. The completed expression plasmids were designated pIG3-HPC (wild-type protein C), pGH41 (T254S), pGH51 (A195G), and pGH94 (L194S).

The pIG3 vector was generated by the insertion of an "internal ribosome entry site" (IRES) (Jackson, et al., *Trends Biochem Sci* 15 (12): 447–83, 1990) and green fluorescent protein (GFP) (Cormack, et al., *Gene* 173: 33–38, 1996) gene into the mammalian expression vector pGTD (Gerlitz, et al., *Biochem J* 295 (Pt 1): 131–40, 1993). When a cDNA of interest is cloned into the multiple cloning site of pIG3, the GBMT promoter (Berg, Nucleic Acids Res 20 (20): 5485–6, 1992) drives expression of a bicistronic mRNA (5'-cDNA-IRES-GFP-3'). Efficient translation of the first cistron is initiated by classical assembly of ribosome subunits on the 5'-methylated cap structure of the mRNA; while the normally inefficient translation of a second cistron is overcome by the IRES sequence which allows for internal ribosome assembly on the mRNA. The coupling of the cDNA and reporter on a single mRNA, translated as separate proteins, allows one to screen for the highest-producing clones on the basis of fluorescence intensity. The expression vector also contains an ampicillin resistance cassette for maintenance of the plasmid in *E. coli*, and a murine DHFR gene with appropriate expression sequences for selection and amplification purposes in mammalian tissue expression.

The adenovirus-transformed Syrian hamster AV12–664 cell line was grown in Dulbecco's modified Eagle's medium supplemented with 10% fetal bovine serum, 50 µg/mL gentamicin, 200 µg/mL Geneticin (G418), and 10 µg/mL vitamin K1. One day prior to transfection; cells were plated at a density of about $10^5$ cells/25 cm$^2$ FspI-linearized plasmids were transfected using either the calcium phosphate method (ProFection, Gibco BRL-Life Technologies) or FuGene-6 (Boehringer Mannheim), following the manufacturer's instructions. Approximately 48 hours after transfection, the medium was replaced with medium containing 250 nM methotrexate for selection. Colonies resistant to methotrexate were pooled 2–3 weeks after applying drug selection and expanded. The pools were subjected to fluorescence activated cell sorting based upon GFP fluorescence intensity (Cormack, 1996), with the most intense 5% of fluorescent cells being retained and expanded. To obtain material for purification, recombinant cells were grown in a modified mixture of Dulbecco's modified Eagle's and Ham's F-12 media (1:3) containing 1 g/mL human insulin, 1 µg/mL human transferrin, and 10 µg/mL vitamin K1. Conditioned media were collected, adjusted to a final concentration of 5 mM benzamidine and 5 mM EDTA, pH 8.0, and protein C was purified via anion-exchange chromatography as described (Yan, et al., *Bio/Technology* 8:655–661, 1990). Purified protein was desalted/concentrated in Ultrafree-CL 30,000 NMWL filtration units (Millipore) using Buffer A (150 mM NaCl, 20 mM Tris-HCl, pH 7.4), and quantitated by Pierce BCA assay using bovine serum albumin (BSA) as the standard.

EXAMPLE 3

Activation of Recombinant Protein C

Complete activation of the zymogen forms of protein C and polypeptides was accomplished by incubation with thrombin-sepharose. Thrombin-sepharose was washed extensively with Buffer A. 200 µL of packed thrombin-sepharose was mixed with 250 µg of protein C in 1 mL of the same buffer and incubated at 37° C. for 4 hours with gentle shaking on a rotating platform. During the course of the incubation, the degree of protein C activation was monitored by briefly pelleting the thrombin-sepharose, and assaying a small aliquot of the supernatant for aPC activity using the chromogenic substrate S-2366 (DiaPharma). Following complete activation, the thrombin-sepharose was pelleted, and the supernatant collected. aPC concentration was verified by Pierce BCA assay, and the aPC was either assayed directly, or frozen in aliquots at −80° C. All polypeptides were analyzed by SDS-PAGE with either Coomassie-blue staining or Western Blot analysis to confirm complete activation (Laemmli, Nature 227:680–685, 1970).

EXAMPLE 4

Functional Characterization

The amidolytic activity of recombinant human aPC polypeptides were determined by hydrolysis of the tripeptide substrates S-2366 (Glu-Pro-Arg-p-nitroanilide), S-2238 (Pip-Pro-Arg-p-nitroanilide), and S-2288 (Ile-Pro-Arg-p-nitroanilide), Table III. The anticoagulant activity is shown as measured clotting time in an aPTT at 500 ng mL$_{-1}$ aPC. Amidolytic activites were measured using the chromogenic substrate S-2366.

Assays were performed at 25° C., in Buffer A containing 1 mg mL$_{-1}$ BSA, 3 mM CaCl$_2$, and 0.5 nM aPC. Reactions (200 µL/well) were performed in a 96-well microtiter plate, and amidolytic activity was measured as the change in absorbance units/min at 405 nm as monitored in a Thermo-Max kinetic micrometer plate reader. Kinetic constants were derived by fitting velocity data at varying substrate concentrations (16 µM to 2 mM) to the Michaelis-Menten equation. Changes in A405 were converted to mmol product using a path length of 0.53 cm (Molecular Devices Technical Applications Bulletin 4–1), and an extinction coefficient for the released p-nitroanilide of 9620 $M^{-1}$ $cm^{-1}$ (Pfleiderer, Methods Enzymol 19:514–521, 1970). Anti-coagulant activity was assessed by measuring the prolongation of clotting time in the activated partial thromboplastin time clotting assay (Helena Laboratories). Clotting reactions were monitored in a ThermoMax kinetic microtiter plate reader, measuring the time to $V_{max}$ in the change in turbidity.

TABLE III

Functional characterization of protein C polypeptides

| Protein | Anticoagulant activity APTT Clotting Time | Amidolytic activity Kcat/Km (mM $s^{-1}$) |
|---|---|---|
| Control | 36 seconds | N/A |
| WT-aPC | 114 seconds | 98 |
| Leu194S | 108 seconds | 84 |
| Ala195G | 120 seconds | 66 |
| Thr254S | 108 seconds | 63 |

EXAMPLE 5

Inactivation of aPC Polypeptides

Figure 3:
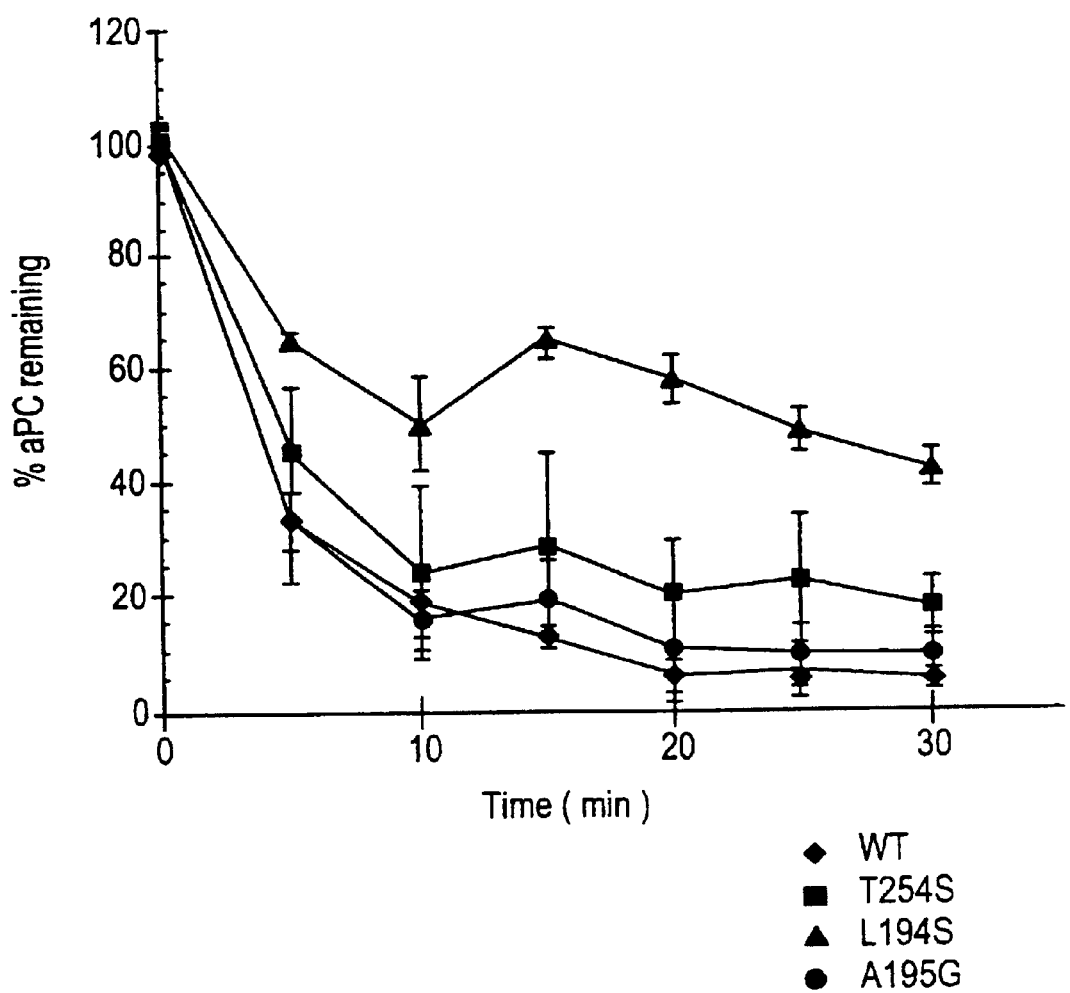

The rates of inactivation of aPC polypeptides were determined by incubating normal human plasma (Helena Labs) with 20 nM aPC (or either polypeptide) at 37° C. (FIG. 1). Plasma concentration was 90% (v/v) in the final reaction buffer containing 150 mM NaCl, 20 mM Tris, pH 7.4, and 1 mg $mL^{-1}$ BSA. Aliquots were removed at selected times, and activity was measured as amidolytic activity using S-2366 at a final concentration of 1 mM. The measured half-lives are summarized in Table IV. To assess the impact of activated protein C polypeptide inactivation by PCI, heparin (10 U $mL^{-1}$), which is known to cause about 100-fold stimulation in the inactivation of aPC by PCI (Heeb, et al., *J Biol Chem* 263 (24): 11613–11616, 1988; Espana, et al., *Thromb Res* 55 (3): 369–84, 1989; Aznar, et al., *Thromb Haemost* 76 (6): 983–988, 1996), was added to a similar reaction (FIG. 3). Inactivation by $\alpha_1$-antitrypsin ($\alpha_1$-AT) was determined by incubation of aPC or derivatives at 20 nM with 40 mM $\alpha_1$-AT (Sigma) in a reaction buffer consisting of 3 mM $CaCl_2$, 150 mM NaCl, 20 mM Tris, pH 7.4, and 1 mg $mL^{-1}$ BSA. Aliquots were removed at selected times, and activity was measured as amidolytic activity using S-2366 at a final concentration of 1 mM.

TABLE IV

Half-lives for inactivation of activated protein C polypeptides in normal human plasma.

| Protein | $t_{1/2}$ (min) | -Fold increase relative to wild-type |
|---|---|---|
| Wild-Type | 28 | 1 |
| Leu194Ser | 180 | 6.5 |
| Leu194Ala | 88 | 3.1 |
| Ala195Gly | 50 | 1.8 |
| Thr254Ser | 50 | 1.8 |
| Leu194Ser/Thr254Ser | 253 | 9.1 |
| Leu194Ala/Thr254Ser | 280 | 10.1 |

EXAMPLE 6

In vivo Pharmacokinetics

Figure 5:
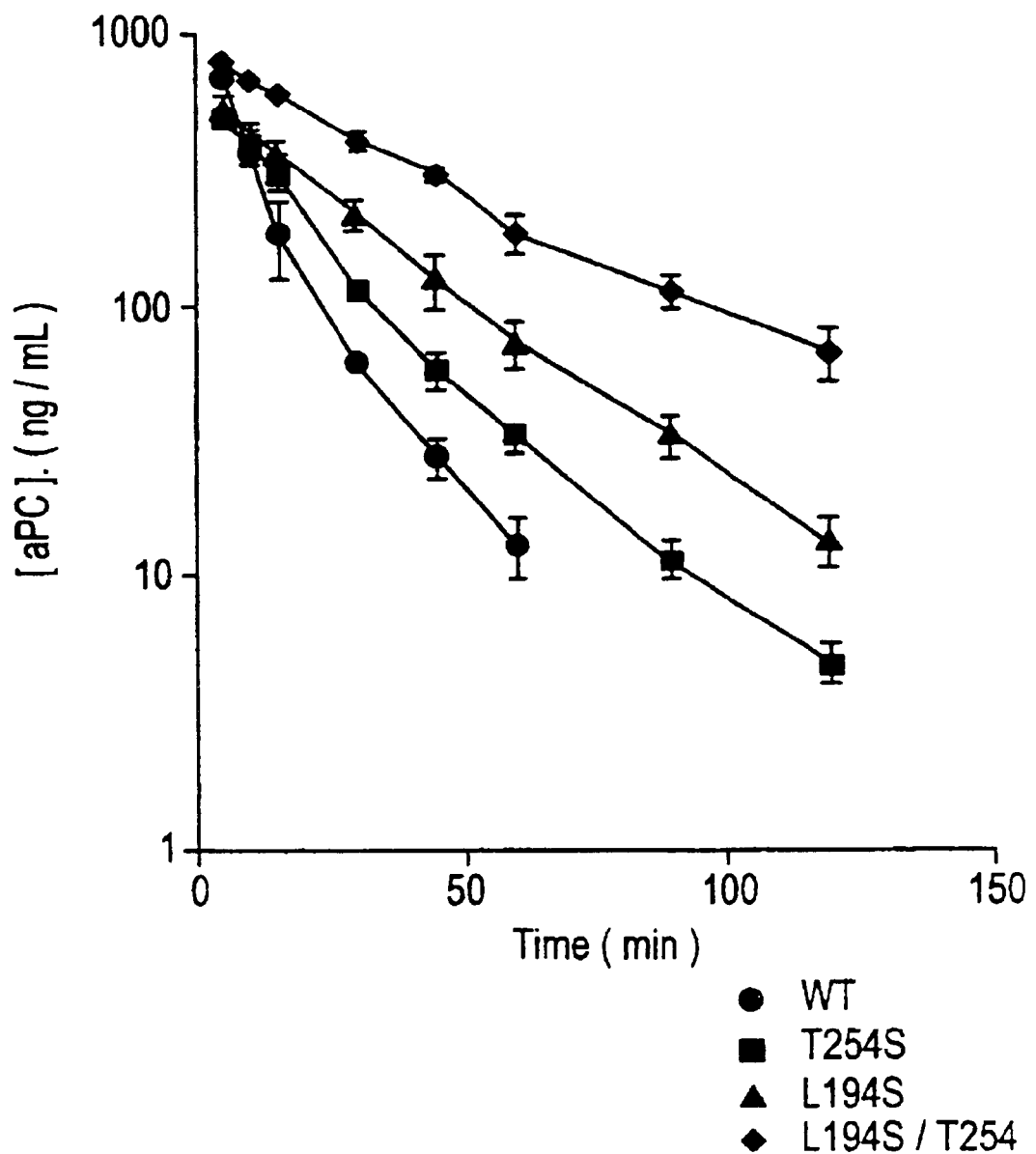

In vivo pharmacokinetic experiments were performed in normal rabbits to verify the observed in vitro effects in half-life as a result of the mutations. A marginal ear vein and a central ear artery was cannulated in the conscious rabbit. Activated protein C polypeptides in buffer A (300 μg/ml) were used to administer a dose of 100 μg/Kg or 0.1 mg/kg bolus through the marginal ear vein catheter. Blood was sampled (0.45 ml) into a syringe containing 0.05 ml of 3.8% citrate containing benzamidine-adjustments were made to compensate for the syringe/needle dead space to yield the final concentration of 1 part citrate/benzamidine: 9 parts blood. Samples were collected 0, 5, 10, 15, 30, 45, 60, 90, 120, 180, 240, 300 and 360 minutes post treatment, spun as soon as convenient after collection, and 200 μl of plasma was aliquoted into 96-well plates. The level of activated protein C polypeptides were determined using an enzyme capture assay (ECA), as described previously (Gruber, et al., *Blood* 79 (9): 2340–2348, 1992), compared to standards ranging from 1 to 250 ng/mL diluted in pooled rabbit plasma. The results for wild-type and Leu194Ser are shown in FIG. 5.

We claim:

1. An isolated and/or recombinant protein C derivative comprising SEQ ID NO: 1, wherein one or more amino acid residues of SEQ ID NO: 1 selected from the group consisting of position 194, 195, 228, 249, 254, 302, or 316; is substituted with an amino acid selected from Ser, Ala, Thr, His, Lys, Arg, Asn, Asp, Flu, Gly, and Gln; provided said position 195 is not Ala and said position 254 is not Thr.

2. The protein C derivative of claim 1, that is more resistant to serpin inactivation in it activated form than wild-type activated human protein C of SEQ ID NO: 2.

3. The protein C derivative of claim 1, wherein said protein C derivative is in its activated form.

4. The protein C derivative of claim 1 comprising SEQ ID NO: 3.

5. The protein of claim 1 comprising SEQ ID NO: 4, wherein Leu at position 194 is replaced with Ser (L194S) and Thr at position 254 is replaced with Ser (T254S).

6. The protein C derivative of claim 1 comprising SEQ ID NO: 5, wherein Leu at position 194 is replaced with Ala (L194A) and Thr at position 254 is replaced with Ser (T254S).

7. A protein C derivative encoded by a polynucleotide computing SEQ ID NO: 8.

8. An isolated and/or recombinant polynucleotide encoding the protein C derivative of claim 5, wherein said polynucleotide comprises SEQ ID NO: 9.

9. An isolated and/or recombinant polynucleotide encoding the protein C derivative of claim 6, wherein said polynucleotide comprises SEQ ID NO: 10.

10. A method of treating vascular occlusive disorders and/or hypercoagulable states comprising administering to a patient in need thereof a pharmaceutically effective amount of a pharmaceutical composition comprising an activated protein C derivative of claim 1 having a greater half-life than wild type activated human protein C of SEQ ID NO: 2.

11. The method of claim 10, wherein said vascular occlusive disorders and/or hypercoagulable states comprise at least one of: sepsis, disseminated intravascular coagulation, purpura fulmination, major trauma, major surgery, burns, adult respiratory distress syndrome, transplantations, deep vein thrombosis, heparin-induced thrombocytopenia, sickle cell disease, thalassernia, viral hemorrhagic fever, thrombotic thrombocytopenic purpura, and/or hemolytic uremic syndrome.

12. A method of treating a thrombotic disorder or disease state comprising administering a pharmaceutically effective amount of a protein C derivative of claim 1 with increased resistance to serpin inactivation, wherein said derivative has an amino acid residue substitution of L194S, L194S:T254S, or L194A:T254S.

13. The method of claim 12 wherein said thrombotic disorder or disease state comprises myocardial infarction, unstable angina, or stroke.

14. A method of treating sepsis comprising administering a pharmaceutically effective amount of a protein C derivative of claim 1 with increased resistance to serpin inactivation in combination with a bacterial permeability increasing protein, wherein said derivative has an amino acid residue substitution of L194S, L194S:T254S, or L194A:T254S.

15. A pharmaceutical composition comprising a protein C derivative of claim 1 in a pharmaceutically acceptable diluent.

16. The pharmaceutical composition of claim 15 wherein said protein C derivative is activated and is more resistant to serpin inactivation and/or has a greater half-life than wild-type activated human protein C of SEQ ID NO: 2.

17. A vector, comprising a polynucleotide sequence of claim 8.

18. A host cell transformed by the vector of claim 17.

19. A vector, comprising a polynucleotide sequence of claim 9.

20. A host cell transformed by the vector of claim 19.

21. An isolated and/or recombinant nucleic acid, comprising a polynucleotide sequence encoding a protein C derivative of claim 1.

22. A vector, comprising a polynucleotide of claim 21.

23. A host cell transformed by the vector of claim 22.

24. A protein C of derivative consisting of the protein C derivative of claim 1 further having one, two, three, four, or five conservative amino acid substitutions.

25. The protein C derivative of claim 24 wherein said protein C derivative is activated.

26. An article of manufacture for human pharmaceutical use comprising: packaging material and a viral comprising a lyophilized activated human protein C derivative of claim 1.

27. The article of manufacture for human pharmaceutical use of claim 26, wherein said packaging comprises a label which indicates that said protein C derivative be administered at a dosage of about 0.01 µg/kg/hr to about 50 µg/kg/hr.

28. An activated human protein C derivative of claim 1 with resistance to inactivation by serpins compared to wild-type protein C produced by the process comprising:
  (a) transforming a host cell with a vector containing nucleic acid encoding a human protein C derivative of claim 1;
  (b) culturing said host cell in a human appropriate for expression of said human protein C derivative;
  (c) isolating said human protein C derivative from the culture medium; and
  (d) activating said human protein C derivative.

29. The activated human protein C derivative of claim 28 wherein said derivative has an amino acid residue substitution of L194S, L194S:T254S, or L194A:T254.

30. The activated human protein C derivative of claim 28 that is produced in a host cell selected from 293 cells or AV12 cells.

31. The protein C derivative of claim 2 which is approximately in the range of from 2–10 times more resistant to serpin inactivation than wild-type activated human protein C.

32. The method of claim 10 wherein said protein C derivative has a substitution/s selected from: L194S, L194S:T254S, and L194A:T254S.

33. The method of claim 10, wherein said protein C derivative has substitution L194S.

34. The method of claim 10, wherein said protein C derivative has substitution L194S:T254S.

35. The method of claim 10, wherein said protein C derivative has substitution L194A:T254S.

36. The pharmaceutical composition of claim 16, wherein said protein C derivative has a substitution from: L194S, L194S:T254S, and L194A:T254S.

37. The pharmaceutical composition of claim 16, wherein said protein C derivative has substitution L194S.

38. The pharmaceutical composition of claim 16, wherein said protein C derivative has substitutions L194S:T254S.

39. The pharmaceutical composition of claim 16, wherein said protein C derivative has substitutions L194A:T254S.

* * * * *